United States Patent [19]
Miller

[11] Patent Number: 5,916,493
[45] Date of Patent: Jun. 29, 1999

[54] HUMIDIFIER SYSTEM

[75] Inventor: Kenneth G. Miller, Orange, Calif.

[73] Assignee: Pegasus Research Corporation, Santa Ana, Calif.

[21] Appl. No.: 08/909,537

[22] Filed: Aug. 12, 1997

[51] Int. Cl.[6] .............................. B01F 3/04; A61M 15/00
[52] U.S. Cl. .............. 261/154; 128/204.13; 128/204.17; 261/104; 261/DIG. 34
[58] Field of Search .............................. 261/99, 104, 107, 261/131, 154, DIG. 4, DIG. 34; 128/203.12, 203.13, 203.14, 204.13, 204.14, 204.17

[56] References Cited

U.S. PATENT DOCUMENTS

| | | | |
|---|---|---|---|
| 3,592,451 | 7/1971 | McDuffee | 261/103 |
| 3,724,180 | 4/1973 | Morton et al. | 55/401 |
| 3,804,280 | 4/1974 | van Amerongen et al. | 215/1 C |
| 3,820,540 | 6/1974 | Hirtz et al. | 128/204.13 |
| 3,846,518 | 11/1974 | McPhee | 261/123 |
| 3,903,216 | 9/1975 | Allan et al. | 261/78.2 |
| 4,110,419 | 8/1978 | Miller | 261/154 |
| 4,225,542 | 9/1980 | Wall et al. | 261/131 |
| 4,419,302 | 12/1983 | Nishino et al. | 128/204.17 |
| 4,454,877 | 6/1984 | Miller et al. | 128/200.21 |
| 4,629,590 | 12/1986 | Bagwell | 261/78.2 |
| 4,652,408 | 3/1987 | Montgomery | 128/204.13 |
| 4,657,713 | 4/1987 | Miller | 261/154 |
| 4,674,494 | 6/1987 | Wiencek | 261/104 |
| 4,879,997 | 11/1989 | Bickford | 128/203.14 |
| 4,911,157 | 3/1990 | Miller | 128/200.21 |
| 5,067,169 | 11/1991 | Chiu | 392/406 |
| 5,195,515 | 3/1993 | Levine | 128/204.17 |
| 5,367,604 | 11/1994 | Murray | 392/394 |
| 5,383,447 | 1/1995 | Lang | 128/204.17 |

*Primary Examiner*—C. Scott Bushey
*Attorney, Agent, or Firm*—Olson & Hierl, Ltd.

[57] ABSTRACT

A humidifier system for producing a humidified and heated breathing gas including a humidifier module having a humidifying chamber with a supply gas inlet, a breathing gas outlet and a heat transfer element. A tube extending between a liquid reservoir and the humidifier module includes therein an elongate liquid absorbing wick whose upper end has a plurality of leaves extending planarly and radially outwardly therefrom into the humidifying chamber into contact with said heat transfer element. Liquid is transported by the wick upwardly into the leaves thereof where it is evaporated and mixed with the supply gas in the humidifying chamber to generate a heated and humidified breathing gas. A vent passage between the humidifying chamber and the liquid reservoir allows the automatic adjustment of the pressure in the reservoir and thus the capillary flow of liquid up the wick in response to a change in the volumetric rate of supply gas so as to provide a humidifier system where the heat and humidity level of the breathing gas are self-regulated.

18 Claims, 3 Drawing Sheets

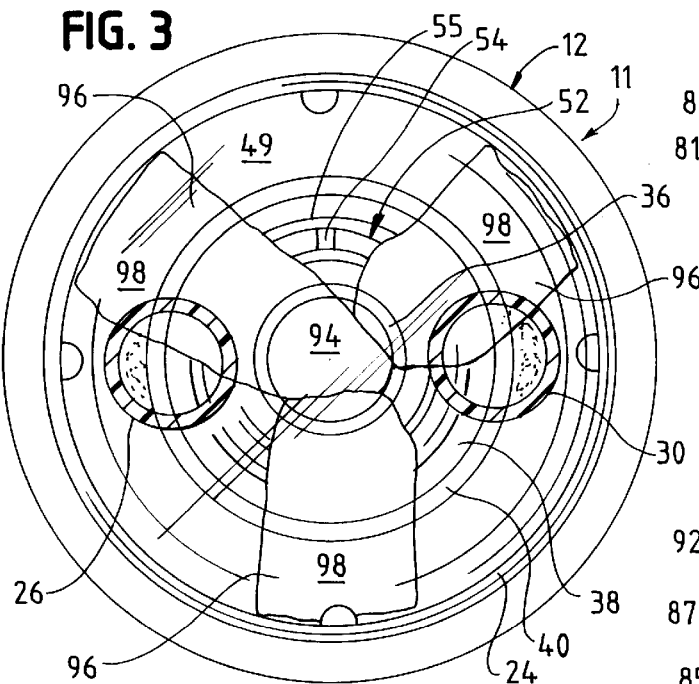
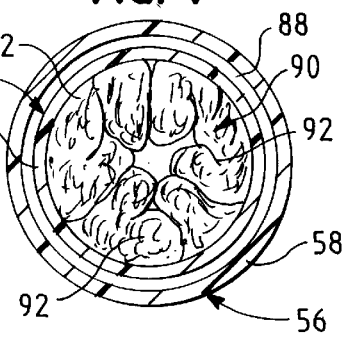
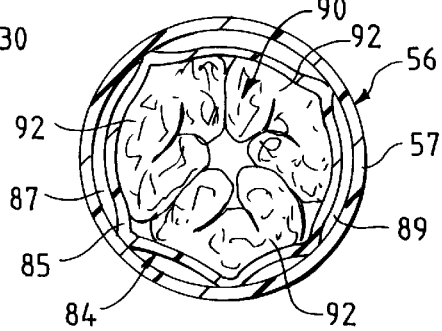
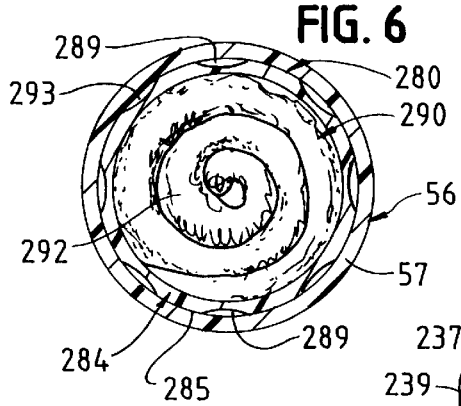
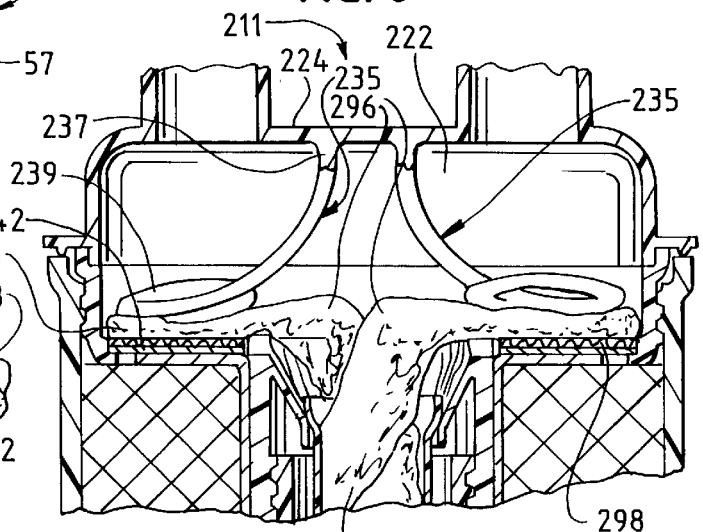
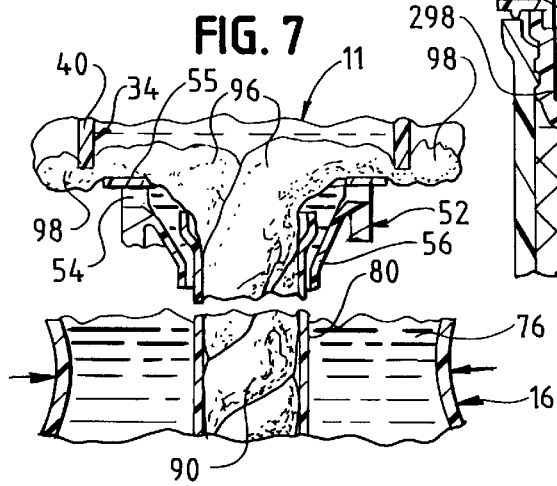

HUMIDIFIER SYSTEM

TECHNICAL FIELD OF THE INVENTION

This invention relates to inhalation therapy devices and, more particularly, to a humidifier system for producing a humidified and heated breathing gas.

BACKGROUND OF THE INVENTION

The administration of oxygen to a patient usually has an adverse drying effect on the patient's respiratory system. Therefore, various humidifying devices have been used to humidify and heat the oxygen being administered to a patient by mixing the oxygen with vaporized water.

A typical humidifier system for inhalation therapy comprises a bottle or the like reservoir containing a sterile liquid such as water, and a humidifier assembly. The humidifier assembly is usually connected to a supply of pressurized oxygen. A heater associated with the humidifier assembly vaporizes the liquid in the bottle and the vaporized liquid is admixed with the oxygen in the humidifying assembly to produce a humidified and heated oxygen stream which is delivered to a patient through an outlet in the humidifier assembly.

A drawback associated with the humidifier heater is that if the oxygen flow to the humidifier is reduced or inadvertently interrupted, the heater has a tendency to provide too much heat to the liquid in the reservoir thus causing the overheating of the liquid and the breathing gas and creating a hazardous condition.

My U.S. Pat. No. 4,911,157 discloses a system for nebulizing and heating a breathing gas in which the heat input to the supply gas is automatically adjusted in response to a change in the volumetric rate of the supply gas so as to avoid any overheating of the breathing gas.

My nebulizer system includes a nebulizer module, a heater module provided with an annular heat transfer element secured to the nebulizer module, and a liquid receptacle removably attached to the heater module. The nebulizer module is connectable to an oxygen supply source, and through an outlet, to an inhalation apparatus. The nebulizer module includes a nebulizing chamber where pressurized oxygen gas, ambient air, and water are combined to form a conically shaped aerosol spray which, in turn, impinges upon the annular heat transfer element operably associated with the heater module. Those particles of the aerosol spray which impinge upon the heat transfer element are volatilized to provide the desired amount of latent heat to the oxygen mixture passing to the patient.

The total flow from the nebulizing chamber may be modulated by the amount of air introduced into the nebulizing chamber. As an example, total flow with no air entrainment averages approximately 7 liters per minute. This flow increases geometrically as the oxygen concentration is diluted by air so that at full air entrainment, the total flow approximates 80 liters per minute. Clearly, not as much heat is required to volatilize the aerosol spray at zero entrainment (pure oxygen) as at full entrainment; thus, the heat output requirement of the heat transfer element can vary considerably.

My nebulizer system provides a self-regulating heat input feature which mitigates the problem of changing heat requirements. By providing substantial axial alignment between the annular heating element and the throat of the nebulizer assembly, the heat output of the heating element is self-regulated as a function of the conical flow pattern exhausted from the throat. Because a smaller flow cone is exhausted from the throat as the entrainment of the nebulizer is reduced, fewer aerosol droplets are impinged upon and vaporized by the heat transfer element. Conversely, as a larger size flow cone is exhausted from the throat as a result of higher entrainment and, thus, increased total flow, more particles strike the heat transfer element. Therefore, the aerosol spray can be maintained at a substantially constant temperature at widely varying air intake rates to the nebulizer system. As such, a greater heat input to the gas stream is automatically provided to match the higher flow rate.

Although my self-regulating nebulizer is suitable in most inhalation therapy applications, there exists applications where a humidifier is more suitable than a nebulizer.

What is thus needed is a humidifier system using a similar heating technique and which, like my nebulizer system, is capable of providing and maintaining an adequate output of breathing gas having a regulated humidity level and temperature with relatively low compliance and relatively small dead space volume.

SUMMARY OF THE INVENTION

The present invention provides a humidifier system for humidifying and efficiently heating a breathing gas to be inhaled by a patient undergoing inhalation therapy in which the heat and humidity input to the supply gas are automatically adjusted in response to a change in the volumetric intake rate of the supply gas so as to avoid any overheating or overhumidifying of the breathing gas.

The humidifier system of the present invention comprises a humidifier assembly including a humidifier module connectable to a gas supply, a breathing apparatus and a liquid reservoir. The humidifier module is isolated from the liquid reservoir and defines a humidifying chamber which includes a gas supply inlet port, a breathing gas outlet port and a heat transfer element. The liquid level in the liquid reservoir is always below the humidifier module, thereby obviating flooding of the humidifier module and thus the danger of patient inhaling liquid water.

A liquid transport conduit extends between the liquid reservoir and the humidifier module for transporting the liquid from the liquid reservoir to the humidifier module. The liquid transport conduit contacts the heat transfer element for evaporating the liquid transported thereby and generating a heated and humidified breathing gas.

The liquid transport conduit comprises a tube with an elongate liquid absorbing wick therein having one end extending into the liquid reservoir and an opposite end in contact with the heat transfer element.

In one embodiment, the wick comprises an elongate rolled sheet of absorbent material such as cotton having one end in the liquid reservoir and an opposite end including a plurality of diametrically opposed leaves extending planarly and radially outwardly therefrom into contact with the heat transfer element.

In another embodiment, the wick comprises a plurality of elongate liquid absorbing strips of cotton or the like which has been twisted together longitudinally. One end of the wick extends into the liquid reservoir and the opposite end includes a plurality of leaves defined by the ends of the plurality of strips comprising the liquid transport conduit. The leaves extend liquid radially outwardly from the wick into contact with the heat transfer element.

The tube includes an outwardly flared upper end which defines a vent passage between the humidifying chamber and the liquid reservoir. The vent passage operates as a check valve which prevents pressurization or depressurization of the liquid reservoir.

In operation, a stream of oxygen or the like supply of a breathing gas is introduced through the inlet port into the humidifying chamber. As the gas stream passes through the chamber, liquid from the reservoir is continually drawn and transported up the wick into the leaves thereof where the liquid is heated and vaporized. The heated liquid vapor is combined with the supply gas in the humidifying chamber to create a heated and humidified breathing gas which is passed to a breathing apparatus through the outlet port.

As described earlier, a drawback associated with current humidifiers is that if the flow of supply gas to the humidifier is reduced or interrupted, the heater provides too much heat and the breathing gas is overheated and overhumidified.

That risk is eliminated in the present invention because the amount of liquid heated at any given time is relatively small compared to the volumetric amount of supply gas introduced into the humidifying chamber. If the volumetric amount of supply gas introduced into the humidifying chamber is reduced, there is a reduction in the local negative pressure in the humidifying chamber which, through the vent passage between the humidifying chamber and the liquid reservoir, causes a drop in the local negative pressure in the reservoir which, in turn, causes a reduction in the amount of liquid transported up by the wick and thus a reduction in the amount of liquid vaporized into the humidifying chamber.

Other features and advantages of the present invention will become readily apparent from the following detailed description, the appended drawings, and the accompanying claims.

BRIEF DESCRIPTION OF THE DRAWINGS

In the drawings:

FIG. 3 is a horizontal plan view taken along the plane 3—3 in FIG. 2;

FIG. 4 is a horizontal cross-sectional view taken along the plane 4—4 in FIG. 1;

FIG. 5 is a horizontal cross-sectional view taken along the plane 5—5 in FIG. 1;

FIG. 6 is a horizontal cross-sectional view taken along the plane 6—6 in FIG. 1 illustrating an alternate embodiment of the tube and the wick of the present invention;

FIG. 7 is a cross-sectional elevational view, partially broken away, illustrating the separation of the tube from the neck of the humidifier module during the priming of the humidifier system; and FIG. 8 is an elevational cross-sectional view, partially broken away, illustrating the interior of an alternate embodiment of the humidifier module of the present invention.

DESCRIPTION OF THE PREFERRED EMBODIMENT

Figure 1:
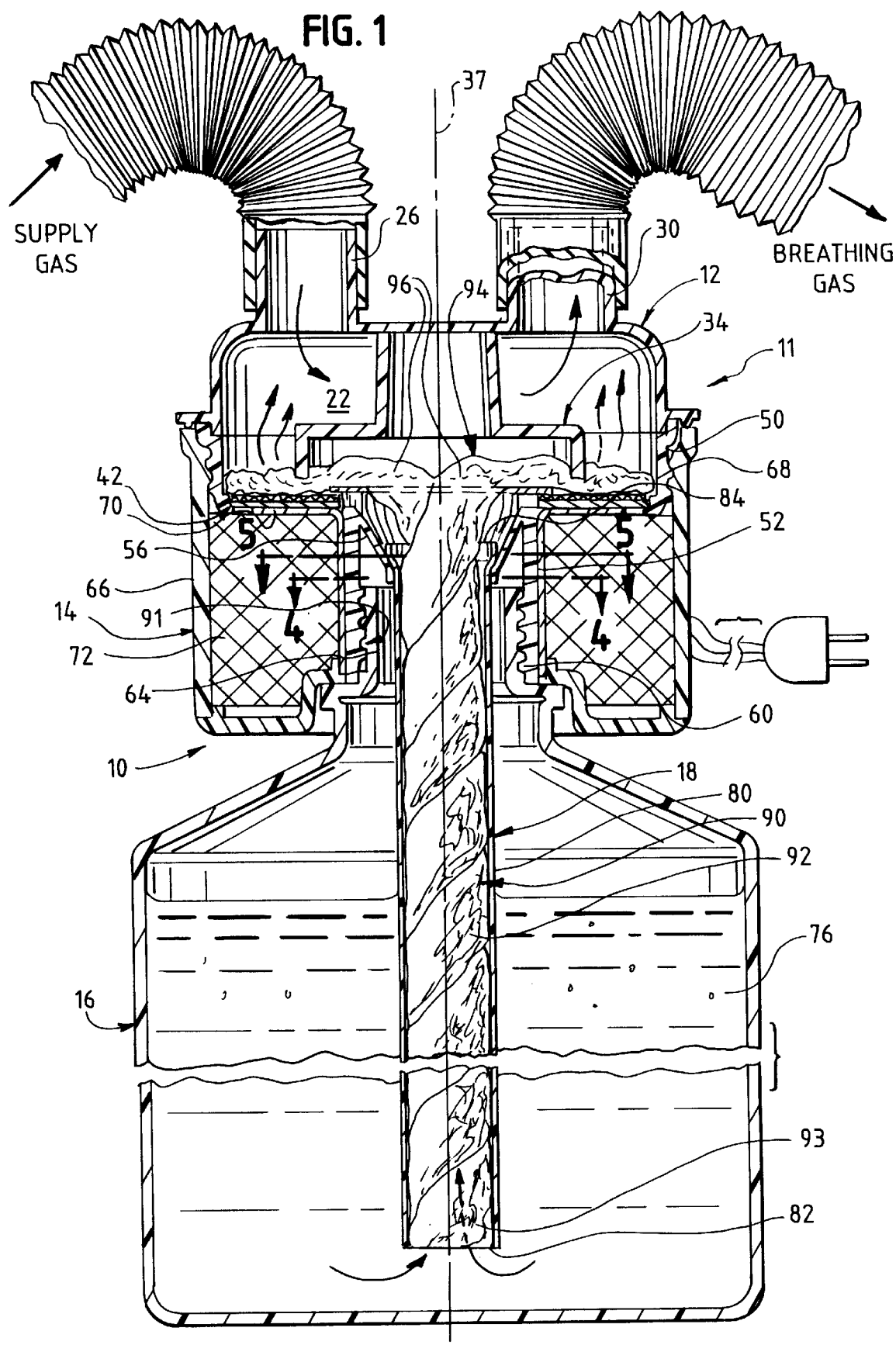
FIG. 1 is cross-sectional elevational view, partially broken away, illustrating a humidifier system embodying the principles of the present invention.

The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

For ease of description, a humidifier system embodying the present invention is described hereinbelow in its usual vertical assembled position as shown in the accompanying drawings and terms such as upper, lower, horizontal, etc., will be used herein with reference to this usual position. However, the humidifier system may be manufactured, stored, transported and sold in orientations other than that described and shown herein.

Figure 2:
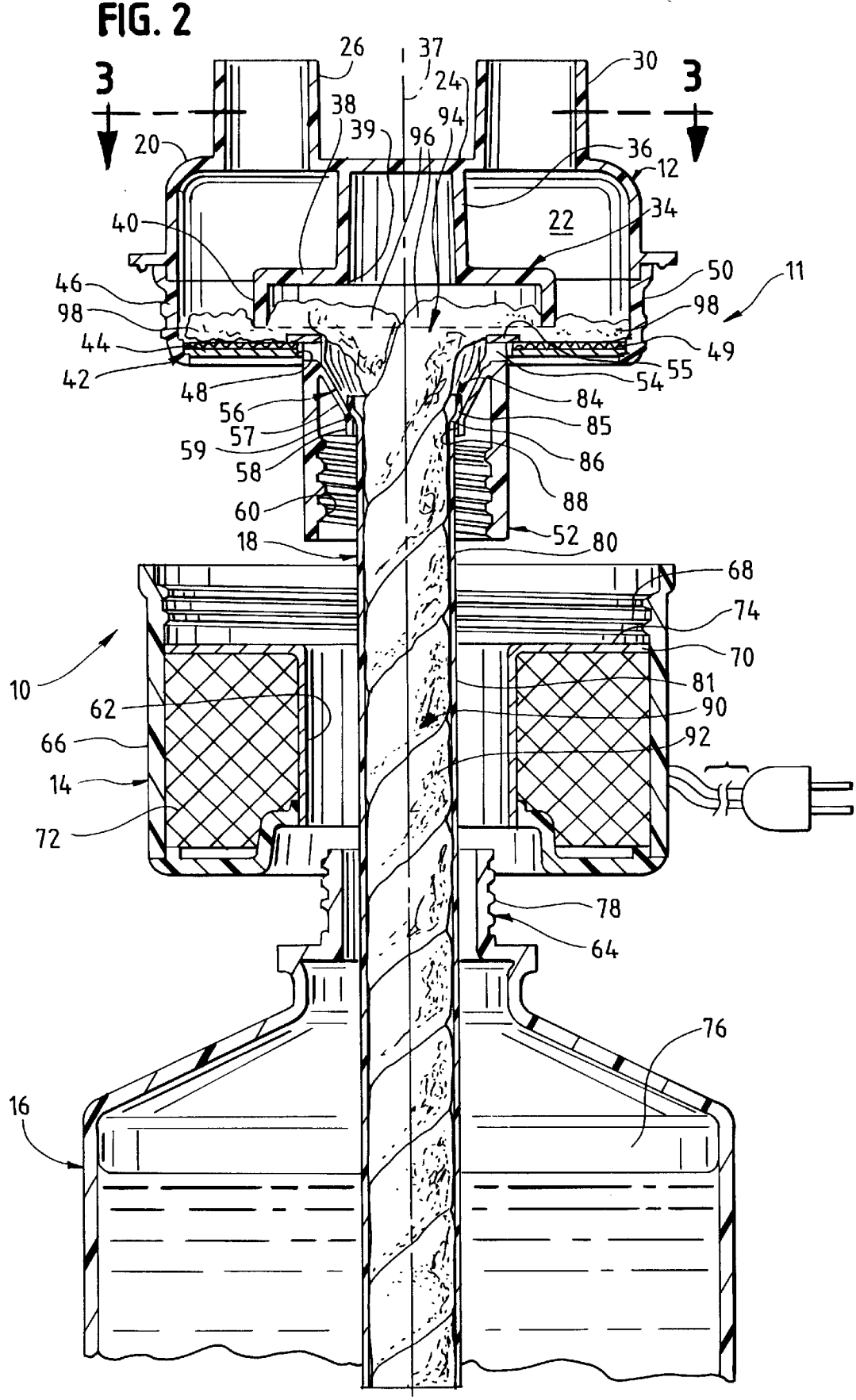
FIG. 2 is an exploded cross-sectional elevational view, partially broken away, of the humidifier system of FIG. 1.

Referring now to the drawings and, more particularly, to FIGS. 1 and 2, there is shown a humidifier device or system 10 according to the present invention comprising a humidifier assembly 11 including a generally shell shaped humidifier module 12 having releasably secured thereto a generally cylindrically shaped heater module 14 and a liquid supply bottle 16. The humidifier assembly 11 also includes an elongate tubular liquid supply or transport conduit 18 extending centrally through the humidifier system 10 and, more particularly, from the supply bottle 16, through the center of the heater module 14 and into the humidifier module 12.

Referring to FIG. 2, the humidifier module 12 is comprised of a bodyshell 20 which defines an interior humidifying chamber 22. The bodyshell 20 includes a flat generally circularly shaped top wall 24 having a tubular inlet port 26 in communication with the humidifying chamber 22 to which is connected a pressurized gas (oxygen) source (not shown) and a tubular outlet port 30 also in communication with the humidifying chamber 22 to which is connected a breathing apparatus (not shown). The inlet and outlet ports 26 and 30 respectively are positioned along the central transverse axis of the humidifier module 12 and are diametrically opposed to each other.

The humidifier module 12 further includes a plate assembly 34 located within the interior of the humidifying chamber 22. Plate assembly 34 includes a hollow tube 36 depending from the interior surface of the top wall 24 of the humidifier module 12 and extending inwardly into the humidifying chamber 22 along the longitudinal axis 37 of the humidifying system 10. An annular and planar unitary plate 38 extends radially outwardly from the lower peripheral edge of the tube 36 and includes a central circular aperture 39 defined by the lower open end of the tube 36. A skirt or wall 40 depends downwardly from, and extends circumferentially about, the lower peripheral annular edge of the plate 38. A heat transfer element 42 is located at the lower end of the humidifier module 12 substantially normal to the longitudinal axis 37 of the humidifier system 10. The heat transfer element 42 includes an annular, planar metal or ceramic disc 44 which is sealed about its peripheral outer edge to a depending cylindrical skirt portion 46 defined by the bodyshell 20 of the humidifier module 12. The disc 44 defines a central circular aperture 48 which is substantially axially aligned with the longitudinal axis 37 of the humidifying system 10 and the central aperture 39 of the annular plate 38. The plate 38 is spaced from and generally parallel to the heat transfer element 42. An annular, substantially planar absorbent disc 49 is seated on and abuts the top surface of the heat transfer element 42. External threading 50 is provided on the skirt portion 46 to allow threaded securement of the humidifier module 12 to the heater module 14.

Still referring to FIG. 2, humidifier module 12 further includes a tubular neck 52 in communication with the humidifying chamber 22 which is sealed to, and depends downwardly from, the central aperture 48 in the disc 44. The neck 52 is aligned axially with, and extends along the length of, the longitudinal axis 37 of the humidifying system 10 and further is positioned concentrically with the central aperture 48 of the disc 44.

A series of diametrically opposed slots 54 (FIG. 3) may be provided at the upper end of the neck 52. A ring 55 overlies the upper peripheral end of the neck 52 and the slots 54 therein.

A funnel like chute 56 depends from the upper end of the neck 52. The chute 56 includes a conical wall 57 converging inwardly from the inner wall of the neck 52, a unitary cylindrical wall 58 extending downwardly from the conical wall 57 and a shoulder 59 defined therebetween.

At its lower end, the neck 52 defines an internally threaded portion 60. More particularly, the length of the neck 52 is sufficient to pass through a central opening 62 in the heater module 14 and threadably engage an upper end of the neck 64 of the supply bottle 16 when the modules comprising the humidifier system 10 are assembled together as shown in FIG. 1.

The reusable heater module 14 includes a cylindrical housing 66. An upper end of the housing 66 defines an internally threaded portion 68 which coacts with the externally threaded portion 50 of the humidifier module 12 in a manner releasably securing the two modules together.

The heater module 14 further includes a heated platen 70, which overlies an electrically controlled heat source 72 and which defines a heated surface 74. The heated surface 74 of the platen 70 is arranged in a heat transfer relationship with the annular disc 44 in the humidifier module 12 when the heater module 14 is releasably secured to the humidifier module 12 as shown in FIG. 1.

The liquid supply bottle 16 defines a reservoir 76 adapted to contain a sterile liquid, such as water, which may be medicated. As illustrated in FIG. 1, the neck 64 of supply bottle 16 includes an externally threaded portion 78 adapted for securement to the internally threaded portion 60 of the neck 52 of the humidifier module 12.

The liquid supply or transport conduit 18 of humidifier assembly 11 includes an elongate plastic tube 80 having a tubular hollow body 81 extending through the neck 52 of humidifier module 12, the central opening 62 in the heater module 14, the neck 64 of the supply bottle 16, and into the reservoir 76 of bottle 16. The tube 80 includes a lower end 82 (FIG. 1) extending into and immersed in the liquid in the reservoir 76 and an upper flared tubular end 84 (FIG. 2). The flared end 84 is defined by a peripheral tubular end wall 85 having a diameter slightly greater than the diameter of the body 81 so as to define a radial shoulder 86 between the end wall 85 and the body 81. The shoulder 86 of the flared end 84 is seated over and abuts the shoulder 59 of the chute 56 so as to support the tube 80 in the neck 52 of the humidifier module 12. In this seating arrangement, the end wall 85 of the tube 80 is spaced from the conical wall 57 of the chute 56 and the body 81 of the tube 80 is spaced from the cylindrical wall 58 of the chute 56 so as to define a pressure equilibration passageway such as passageway 88 (FIG. 4) between the tube 80 and the chute 56.

As shown in FIG. 5, the flared end wall 85 of the tube 80 is scalloped so as to define a plurality of relatively small optional spaces or apertures 89, between the shoulders 59 and 86 of the chute 54 and the flared end 84 of the tube 80 respectively, which communicate with the passageway 88 to define pressure equilibration passage 91 between the humidifying chamber 22 and the liquid reservoir 76. The size of apertures 89 is no larger than what is needed to equalize the pressure in chamber 22 and liquid reservoir 76. Spaces or apertures 89 can be omitted if pressure equilibration can be achieved through wick 90 or by means of surface irregularities of flared end wall 85.

In an alternate embodiment of the tube 280 as shown in FIG. 6, the flared end wall 285 of the tube 280 includes a plurality of circumferentially extending ridges 293 which also define a plurality of small passageways 289 between the chute 56 and the flared end 284 of the tube 280, respectively.

The liquid supply or transport conduit 18 further includes an elongate liquid absorbing member or wick 90 which extends through the interior of the tube 90. In one embodiment, as been shown in FIGS. 4 and 5, the wick 90 comprises a plurality of elongate longitudinal strips 92 of absorbing material such as cotton or the like which have been twisted together longitudinally as shown in FIG. 2. In an alternate embodiment as shown in FIG. 6, the wick 290 comprises an elongate sheet 292 of absorbing material such as cotton or the like which has been rolled up.

The wick 90 includes a lower planar and annular end 93 (FIG. 1) which is generally flush with the lower end 82 of the tube 80 and is thus immersed in the liquid in the reservoir 76.

The wick 90 also includes an upper end 94 having a plurality of diametrically opposed leaves 96. In the embodiment of FIGS. 1–5 where the wick 90 comprises a plurality of cotton strips 92 twisted together, the leaves 96 are defined by the upper peripheral ends of the strips 92. In the embodiment of FIG. 6 where the wick 290 is comprised of a rolled sheet 291 of cotton material, the leaves are formed by cutting the upper peripheral end of the sheet 292 into three pie shaped sections and then pulling the cut sections back away from the rolled sheet 292.

The leaves 96 extend from the end 94 of the wick 90 planarly and radially outwardly into the humidifying chamber 22 from the longitudinal axis 37 of the humidifier module 12. In particular, the leaves 96 are positioned between and in contact with the skirt 40 of the plate 38 on one side and the absorbent disc 49 overlying the heat transfer element 42 on the lower side. Each of the leaves 96 includes a tip portion 98 which extends beyond the skirt 40 of the plate 38 to the outer periphery of the humidifying module 12.

According to the invention, the plate 38 and, more particularly, the skirt 40 thereof, holds the leaves 96 in contact with the heat transfer element 42 so as to maximize the transfer of heat from the heat transfer element 42 to the leaves 96 as described below.

Referring to FIG. 8, in yet another embodiment, the plate 38 shown in FIG. 2 can be substituted with any other suitable type of assembly for holding the leaves 296 against the heat transfer element 242 such as spring assemblies 235 in the humidifying chamber 222. Each of the spring assemblies 235 includes an upper end 237 abutting the bottom of the top wall 224 of the humidifying chamber 222 and a lower looped end 239 which is abutted against the tip 298 of the respective leafs 296 so as to hold the respective leafs 296 against the heat transfer element 242.

Referring back to FIGS. 4 and 5, the wick 90 can optionally include a central aperture 100 extending therethrough along the longitudinal axis thereof which defines an additional vent passage between the humidifying chamber 22 and the reservoir 76.

In operation, and referring to FIG. 2, the wick 90 must initially be primed. This may be accomplished by inverting the humidifier system 10 or by squeezing the supply bottle 16 to cause the liquid in the reservoir 76 to be thoroughly absorbed into the wick 90 and cause the unseating of the tube 80 from the chute 54 which, in turn, causes the liquid to travel into the upper end of the neck 52 of the humidifying chamber 22 and into the bottom end of the humidifying chamber 22 where the liquid is absorbed by the leaves 96 of the wick 90. Alternatively, the wick 90 can be primed by pouring about 30 ml of the liquid into the humidifying chamber 22 through either the inlet or outlet ports 26 and 30 respectively.

After the wick 90 has been primed, a stream of oxygen or the like oxygen-bearing supply gas is introduced through the inlet port 26 into the humidifying chamber 22. As the gas stream passes through the inlet port 26, capillary action allows liquid from the reservoir 76 to be continually transported up the wick 90 and into the leaves 96 thereof where the liquid is vaporized as a result of the transfer of heat from the heat transfer element 42 to the liquid in the leaves 96. The heated vapor is combined with the supply gas in the humidifying chamber 22 to create a heated and humidified breathing gas which is passed to the breathing apparatus through the outlet port 30. Any coalesced water formed on the disc 44 is fed into the drain channels defined by the slots 54 in the neck 52, through the vent opening 91 and then back into the reservoir 76.

As mentioned earlier, a drawback associated with current humidifiers is that if the oxygen flow to the humidifier is reduced or interrupted, the heater provides too much heat and the breathing gas is overheated and overhumidified.

The present invention eliminates the risk of overheating and overhumidifying because the amount of liquid which is vaporized is dependent upon the volumetric amount of supply gas introduced into the humidifying chamber 22. For example, if the volumetric rate of supply gas introduced into the humidifying chamber 22 is reduced, the local negative pressure in the reservoir 76 is reduced causing a reduction in the amount of liquid carried up through the wick 90, which causes a reduction in the amount of liquid absorbed in the leaves 96 of the wick 90 and thus a reduction in the amount of liquid which is vaporized into the humidifying chamber 22. Thus, a reduced heat and humidity output is automatically obtained to match the reduced flow rate thereby providing the self-regulating feature of the present invention.

For another example, if the flow of supply gas is altogether interrupted, there will be no pressure created in the reservoir 76, no liquid will be drawn up the wick 90 and thus there will be no liquid vaporized except for the liquid already at the tips 98 of the leaves 96 of the wick 90 at the moment the flow of supply gas is interrupted.

In summary, the breathing gas is advantageously maintained at a substantially constant temperature and humidity level regardless of any supply gas intake adjustments. Preferably, the breathing gas is maintained at a temperature lower than body temperature. In particular, it has been determined that the maximum output temperatures at the patient end of a six foot hose at a room ambient temperature of 24° C. should be as follows:

| Minute Supply Gas Volume, liters per minute (Avg. Flow) | Breathing Gas Temperature |
| --- | --- |
| 5 | 37° C. |
| 10 | 34° C. |
| 15 | 32° C. |

From the foregoing, it will be observed that numerous modifications and variations can be effected without departing from the true spirit and scope of the novel concepts of the present invention. It will be appreciated that the present disclosure is intended as an exemplification of the invention, and is not intended to limit the invention to the specific embodiments illustrated. The disclosure is intended to cover by the appended claims all such modifications as fall within the scope of the claims.

I claim:

1. A humidifier assembly for use in a humidifier system including a liquid reservoir, the humidifier assembly comprising:

a humidifier module connectable to a gas supply, a breathing apparatus and the liquid reservoir, said humidifier module defining a humidifying chamber including a gas supply inlet port and a breathing gas outlet port, said humidifier module further including a heat transfer element in communication with said humidifying chamber; and a liquid transport conduit extending between the liquid reservoir and said humidifier module for transporting the liquid from said liquid reservoir to said humidifier module, said liquid transport conduit extending radially outwardly into contact with said heat transfer element for evaporating the liquid and generating a heated and humidified breathing gas.

2. The humidifier assembly of claim 1 wherein said liquid transport conduit comprises an elongate liquid absorbing member having one end extending into the liquid in said reservoir and an opposite end contacting said heat transfer element.

3. A humidifier assembly for use in a humidifier system including a liquid reservoir, the humidifier assembly comprising:

a humidifier module connectable to a gas supply a breathing apparatus and the liquid reservoir, said humidifier module defining a humidifying chamber including a gas supply inlet port and a breathing gas outlet port, said humidifier module further including an annular heat transfer element in communication with said humidifying chamber; and a liquid transport conduit extending between the liquid reservoir and said humidifier module for transporting the liquid from said liquid reservoir to said humidifier module, said liquid transport conduit comprising a liquid absorbing member having opposite ends, one of the ends extending into the liquid reservoir and the other end including a plurality of planar leaves in contact with said heat transfer element for evaporating the liquid and generating a heated and humidified breathing gas.

4. The humidifier assembly of claim 3 wherein said humidifier module includes a neck depending therefrom having therein an inwardly coverging chute in communication with said humidifying chamber, said liquid transport conduit extending through an elongate tube, said tube including an upper flared end seated on said chute and a lower end extending into the liquid reservoir, said end of said liquid absorbing member extending into the liquid reservoir being generally flush with the lower end of said tube and said other end of said liquid absorbing member including said plurality of leaves extending planarly and radially outwardly from the upper flared end of said tube into contact with said heat transfer element.

5. The humidifier assembly of claim 4 wherein the upper flared end of said tube includes a plurality of ridges defining a plurality of openings defining a vent passage between said humidifying chamber and said liquid reservoir.

6. The humidifier assembly of claim 4 wherein the upper flared end of said tube is scalloped so as to define a plurality of defining a vent passage between said humidifying chamber and said liquid reservoir.

7. A humidifier assembly for use in a humidifier system including a liquid reservoir, the humidifier assembly comprising:

a humidifier module connectable to a gas supply, a breathing apparatus and the liquid reservoir, said humidifier module defining a humidifying chamber including a gas supply inlet port and a breathing gas outlet port, said humidifier module further including a heat transfer element in communication with said humidifying chamber; and a liquid conduit extending between the liquid reservoir and said humidifier module for transporting the liquid from said liquid reservoir to said humidifier module, said liquid transport conduit comprising a liquid absorbing member having opposite ends, one of the ends extending into the liquid reservoir and the opposite end including a plurality of planar strips in contact with said heat transfer element for evaporating the liquid and generating a heated and humidified breathing gas, said humidifying chamber further including a plate therein spaced from said heat transfer element, said planar strips of said liquid absorbing member being disposed between said plate and said heat transfer element.

8. A humidifier assembly for use in a humidifier system including a liquid reservoir, the humidifier assembly comprising:

a humidifier module connectable to a gas supply, a breathing apparatus and the liquid reservoir, said humidifier module defining a humidifying chamber including a gas supply inlet port and a breathing gas outlet port, said humidifier module further including a heat transfer element in communication with said humidifying chamber; and a liquid transport conduit extending between the liquid reservoir and said humidifier module for transporting the liquid from said liquid reservoir to said humidifier module, said liquid transport conduit comprising an elongate rolled sheet of cotton material, said rolled sheet having one end in said liquid reservoir and an opposite end including a plurality of diametrically opposed sheet strips extending planarly and radially outwardly therefrom and in contact with said heat transfer element for evaporating the liquid and generating a heated and humidified breathing gas.

9. A humidifier assembly for use in a humidifier system including a liquid reservoir, the humidifier assembly comprising:

a humidifier module connectable to a gas supply, a breathing apparatus and the liquid reservoir, said humidifier module defining a humidifying chamber including a gas supply inlet port and a breathing gas outlet port, said humidifier module further including a heat transfer element in communication with said humidifying chamber; and a liquid transport conduit extending between the liquid reservoir and said humidifier module for transporting the liquid from said liquid reservoir to said humidifier module, said liquid transport conduit comprising a plurality of elongate liquid absorbing strips twisted together to define a wick, one end of the wick extending into said liquid reservoir and the opposite end including a plurality of leaves defined by said plurality of strips in contact with said heat transfer element for evaporating the liquid and generating a heated and humidified breathing gas.

10. The humidifying assembly of claim 1 wherein said liquid transport conduit comprises an elongate liquid absorbing member having one end in said liquid reservoir and an opposite end in contact with said heat transfer element, said liquid absorbing member further including a central aperture extending longitudinally therethrough and defining a vent passage between said humidifying chamber and said liquid reservoir.

11. A humidifier assembly for use in a humidifier system including a liquid supply bottle and a heater module, the humidifier assembly comprising:

a humidifier module including a humidifying chamber having a supply gas inlet, a breathing gas outlet, and an annular heat transfer element in communication with said humidifying chamber and the heater module;

an elongate liquid absorbing wick having one end extending into the liquid supply bottle and an opposite end extending into said humidifying chamber and including a plurality of planar and radially outwardly extending leaves in contact with said heat transfer element;

whereby the liquid absorbed in said leaves of said wick is evaporated therefrom for humidifying the gas supply in said humidifying chamber and generating a heated and humidified breathing gas.

12. The humidifier assembly of claim 11 further comprising a planar plate in said humidifying chamber for holding said planar leaves of said wick against said heat transfer element.

13. The humidifying assembly of claim 11 wherein said humidifier module includes a top wall and a plate assembly therein for holding said leaves against said heat transfer element, said plate assembly including a tube extending inwardly from said top wall of said humidifier module into said humidifying chamber and a planar and annular plate extending radially outwardly from the lower periphery of said tube, said plate being spaced from and parallel to said heat transfer element, said leaves of said wick being disposed between and in contact with said plate and said heat transfer element.

14. The humidifying assembly of claim 11 further comprising a spring in said humidifying chamber for holding said leaves of said wick against said heat transfer element.

15. The humidifying assembly of claim 11 wherein said humidifier module includes a top wall and a plurality of springs in said humidifying chamber for holding said leaves of said wick against said heat transfer element, each of said springs including one end abutting said top wall of said humidifier module and a opposite end holding each of said leaves respectively of said wick in contact with said heat transfer element.

16. A humidifier system for a breathing apparatus comprising:

a humidifier module including a humidifying chamber having a supply gas inlet and a breathing gas outlet, an annular heat transfer element, and a concentric neck depending therefrom and having therein an inwardly converging chute in communication with said humidifying chamber;

a liquid reservoir in communication with said humidifier module;

a heater module in communication with said heat transfer element; and a tube extending between said liquid reservoir and said humidifier module through said heater module and said neck, said tube including therein an elongate liquid absorbing member and a flared upper end seated over said chute in said neck, said flared end of said tube including ridges therein defining a vent passage in said neck between said humidifying chamber and said liquid reservoir, said liquid absorbing member including an upper end with a plurality of strips extending planarly and radially outwardly therefrom into contact with said heat transfer element;

whereby the liquid absorbed in said strips of said liquid absorbing member is evaporated therefrom for humidifying the gas supply in said humidifying chamber and generating a heated and humidified breathing gas.

17. The humidifying system of claim 16 wherein said liquid absorbing member comprises a plurality of longitudinally twisted elongate strips of absorbent material.

18. The humidifying system of claim 16 wherein said liquid absorbing member comprises an elongate rolled sheet of absorbent material.

* * * * *